(12) United States Patent
Nagamine et al.

(10) Patent No.: US 10,822,431 B2
(45) Date of Patent: Nov. 3, 2020

(54) FUCOIDAN PREPARATION, ZINC-BOUND FUCOIDAN AND USE THEREOF

(71) Applicant: South Product Ltd., Uruma-shi (JP)

(72) Inventors: Takeaki Nagamine, Okinawa (JP); Masahiko Iha, Okinawa (JP); Kizuku Kadena, Okinawa (JP)

(73) Assignee: South Product Ltd., Uruma (JP)

( * ) Notice: Subject to any disclaimer, the term of this patent is extended or adjusted under 35 U.S.C. 154(b) by 0 days.

(21) Appl. No.: 16/060,464

(22) PCT Filed: Dec. 11, 2015

(86) PCT No.: PCT/JP2015/084773
§ 371 (c)(1),
(2) Date: Jun. 8, 2018

(87) PCT Pub. No.: WO2017/098653
PCT Pub. Date: Jun. 15, 2017

(65) Prior Publication Data
US 2019/0002595 A1 Jan. 3, 2019

(51) Int. Cl.
*C08B 37/00* (2006.01)
*A61P 3/06* (2006.01)
*A61P 29/00* (2006.01)
*A61P 1/04* (2006.01)
*A61P 35/00* (2006.01)

(52) U.S. Cl.
CPC ............ *C08B 37/0063* (2013.01); *A61P 1/04* (2018.01); *A61P 3/06* (2018.01); *A61P 29/00* (2018.01); *A61P 35/00* (2018.01)

(58) Field of Classification Search
CPC ........ C08B 37/0063; A61P 1/04; A61P 35/00; A61P 29/00; A61P 3/06
USPC ......................................................... 514/62
See application file for complete search history.

(56) References Cited

U.S. PATENT DOCUMENTS

2007/0224215 A1* 9/2007 Buckman ................. A61K 9/48
424/195.17

FOREIGN PATENT DOCUMENTS

| JP | 2006-83285 A | | 3/2006 |
| JP | 2006-306897 A | | 11/2006 |
| JP | 2011-98899 A | | 5/2011 |
| JP | 2012067023 A | * | 4/2012 |
| JP | 5764854 B2 | | 8/2015 |

OTHER PUBLICATIONS

Matsuoka et al.; JP 2012067023 A; Apr. 5, 2012 (Machine-English Translation).*
Paskins-Hurlburt et al. (Bot. Mar., 21, 13-22, (1978).*
International Search Report dated Jan. 12, 2016 in PCT/JP2015/084773 filed Dec. 11, 2015.
S. Matsumoto et al., "Fucoidan derived from *Cladosiphon okamuranus Tokida* ameliorates murine chronic colitis through the downregulation of interleukin-6 production on colonic epithelial cells", Clinical and Experimental Immunology, 2004, vol. 136, pp. 432-439.
H. Shibata et al., "Properties of fucoidan from *Cladosiphon okamuranus* tokida in gastric mucosal protection", BioFactors, 2000, vol. 11, pp. 235-245.
T. Sone et al., "Anti-inflammatory activity of *Cladosiphon okamuranus Tokida* extract", Fragrance Journal, Dec. 2001. 7 total pages (with English abstract).
T. Nagamine et al., "Inhibitory Effect of Fucoidan on Huh7 Hepatoma Cells Through Downregulation of CXCL12", Nutrition and Cancer, 2009, vol. 61, No. 3, pp. 340-347.

* cited by examiner

*Primary Examiner* — Shaojia A Jiang
*Assistant Examiner* — Michael C Henry
(74) *Attorney, Agent, or Firm* — Oblon, McClelland, Maier & Neustadt, L.L.P.

(57) ABSTRACT

Provided is a technique for enhancing the absorption of fucoidan into the body and elevate various effects of fucoidan by using a fucoidan preparation that is characterized by containing fucoidan and zinc and the ratio of zinc to fucoidan being 0.005% or greater.

8 Claims, 3 Drawing Sheets

FUCOIDAN PREPARATION, ZINC-BOUND FUCOIDAN AND USE THEREOF

TECHNICAL FIELD

The present invention relates to a preparation having enhanced fucoidan effect by blending zinc, a zinc-bound fucoidan and use thereof.

BACKGROUND ART

It is known that fucoidan is a polysaccharide peculiar in brown algae and has sulfated fucose in constituent saccharides; however, its structure varies depending on the type of brown algae. For example, among the fucoidans, fucoidan derived from *Cladosiphon okamuranus* (scientific name: *Cladosiphon okamuranus* TOKIDA) is one in which, as shown in the following formula, one molecule of glucuronic acid is bound to six molecules of fucose taking α-1,3 linked fucose as the main chain, and half of the fucose is sulfated.

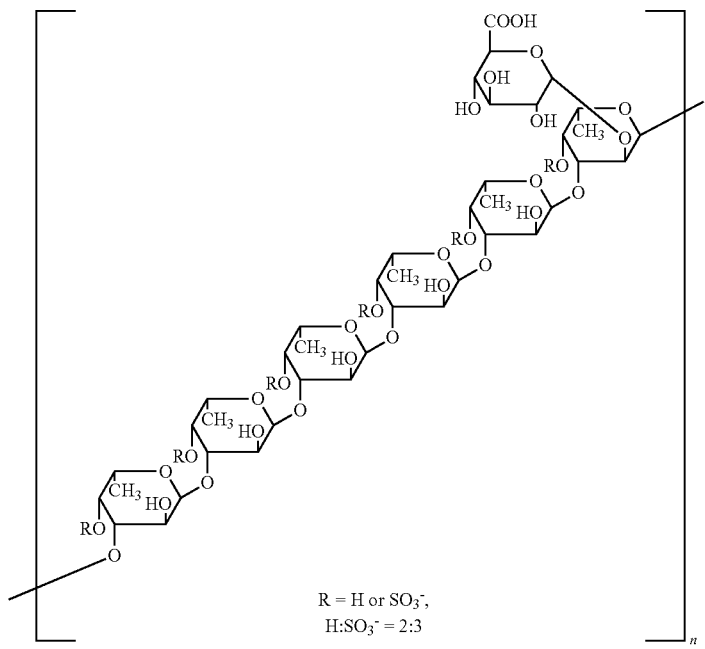

[Chem. 1]

Anti-ulcer activity, anti-inflammatory activity, intestine-regulating activity, antitumor activity, cholesterol down-regulation effect and the like in fucoidan derived from *Cladosiphon okamuranus* have been reported (NPLs 1 to 4).

In recent years, the applicant has been constructing an ELISA system utilizing the antibody of *Cladosiphon okamuranus* fucoidan and reporting a technique for accurately measuring *Cladosiphon okamuranus* fucoidan in blood and tissues by this ELISA system (PTL 1). After *Cladosiphon okamuranus* fucoidan was actually administered, the concentration of *Cladosiphon okamuranus* fucoidan in blood and tissues was measured and it was confirmed that *Cladosiphon okamuranus* fucoidan is indeed absorbed into the body. However, it was also found that it is important to increase the amount of absorption in order to enhance various effects of *Cladosiphon okamuranus* fucoidan. Increasing the amount of absorption is an important issue common to all fucoidans, not only *Cladosiphon okamuranus* fucoidan; however, such technique has not been reported yet.

CITATION LIST

Patent Literature

PTL 1: JP-B-5764854

Non-Patent Literature

NPL 1: Matsumoto S, et al. Fucoidan derived from *Cladosiphon okamuranus* Tokita ameriorates murine chronic colitis through the down-regulation of interleukin-6 production on colonic epithelial cells. Clin Exp Immunol 2004, 136; 432-439.

NPL 2: Shibata H, et al. Properties of fucoidan from *Cladosiphon okamuranus* tokita in gastric mucosal protection. BioFactors 2000, 11; 235-245.

NPL 3: SONE Toshiro, et al. Anti-inflammatory activity of *Cladosiphon okamuranus*. FRAGRANCE Journal 2001, 12; 871-892.

[NPL 4] Nagamine T, et al. Inhibitory effect of fucoidan on Huh7 hepatoma cells through downregulation of CXCL12. Nutr Cancer 2009, 61; 340-347.

SUMMARY OF INVENTION

Technical Problem

Accordingly, an object of the invention is to enhance the absorption of fucoidan into the body and enhance various effects of fucoidan.

Solution to Problem

The inventors have found that, as a result of intensive research to solve the aforementioned problem, by combining fucoidan and zinc, the absorption of fucoidan into the body is enhanced and as a result, various effects of fucoidan are also enhanced. Moreover, the inventors have found that the absorption of fucoidan into the body is particularly enhanced by using a zinc-bound fucoidan in which zinc is bound to a sulfate group of fucoidan, and as a result, various effects of fucoidan become particularly high, and have completed the invention.

That is, the invention is a fucoidan preparation containing fucoidan and zinc, wherein zinc is 0.005% or more with respect to fucoidan.

Further, the invention is a zinc-bound fucoidan, wherein zinc is bound to a sulfate group of the fucoidan.

Moreover, the invention is a food or beverage containing the zinc-bound fucoidan.

Advantageous Effects of Invention

The fucoidan preparation of the invention can enhance the absorption of fucoidan into the body.

Therefore, in the fucoidan preparation of the invention, anti-ulcer activity, anti-inflammatory activity, intestine-regulating activity, antitumor activity and cholesterol down-regulation effect of *Cladosiphon okamuranus* fucoidan are higher than those of conventional ones.

DESCRIPTION OF EMBODIMENTS

Figure 1:
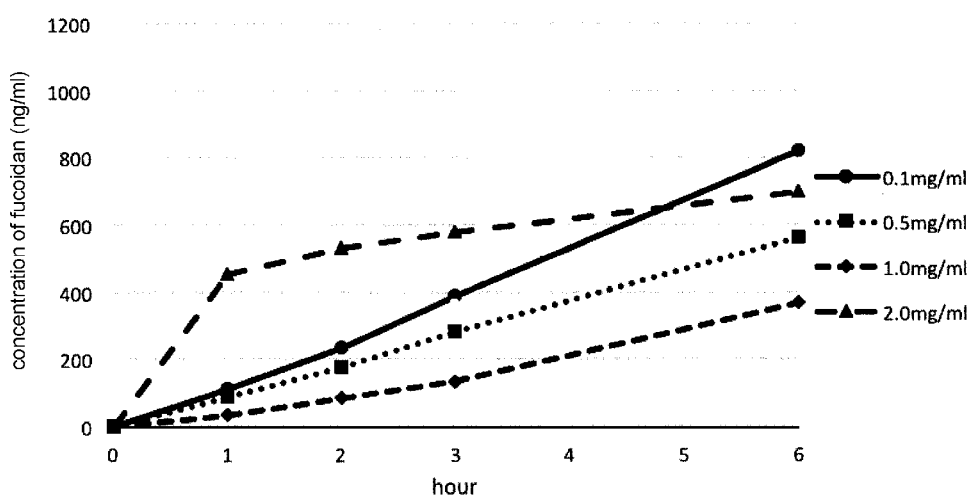
FIG. 1 is a result of absorption test of *Cladosiphon okamuranus* fucoidan (Test Example 1).

The fucoidan preparation of the invention (hereinafter referred to as "the preparation of the invention") contains fucoidan and zinc, and zinc is 0.005% or more, preferably 0.01% or more, more preferably 0.1% or more, particularly preferably 0.5% or more with respect to 1 of fucoidan in terms of mass. The fucoidan contained in the preparation of the invention originally contains about 0.0001 to 0.002% of zinc; however, the amount of zinc contained in the preparation of the invention is larger.

The origin of the fucoidan contained in the preparation of the invention is not particularly limited, and examples include those derived from seaweed of Phaeophyceae such as *Cladosiphon okamuranus, Undaria pinnatifida, Sargassum horneri* (Turner) C. Agardh, *Laminaria Japonica* Arechoug, *Fucus distichus* and *Sargassum fulvellum*. For these fucoidans, those commercially available from Funakoshi Co., Ltd. and the like, those extracted by a method described in the literature (M. Nagaoka, et al.: Structural study of fucoidan from *Cladosiphon okamuranus* TOKIDA. Glycoconjugate Journal 16: 19-26, 1999) and the like can be used without particular limitation. Moreover, fucoidan may be hydrolyzed with an acid such as hydrochloric acid.

The preparation of the invention is not particularly limited as long as the preparation contains fucoidan and zinc and zinc is in the aforementioned amount, and the composition of the preparation of the invention includes, for example, a preparation containing a zinc-bound fucoidan in which zinc is bound to a sulfate group of fucoidan, and a preparation combining fucoidan and zinc. In these preparations, the preparation containing a zinc-bound fucoidan in which zinc is bound to a sulfate group of fucoidan is preferable because it has high absorption into the body and high effect.

The zinc-bound fucoidan in which zinc is bound to a sulfate group of fucoidan can be prepared by preparing a solution containing fucoidan and having zinc bound to the sulfate group of fucoidan by ion exchange.

The fucoidan used in the preparation of the zinc-bound fucoidan is not particularly limited as long as it is the fucoidan described above. However, it is preferable to use fucoidan derived from *Cladosiphon okamuranus* considering the ease of acquisition, high effect and the like.

The solution containing fucoidan used above is not particularly limited. For example, it may be a solution in which purified fucoidan is dissolved in water or the like, or a solution prepared by extracting brown algae containing fucoidan such as *Cladosiphon okamuranus* with a weak acidic solution or the like and removing insoluble substances. The content of fucoidan in the solution is not particularly limited, for example, 0.1 to 5 mass %, preferably 1 to 3 mass %.

In the preparation of the zinc-bound fucoidan, the method of ion exchange is not particularly limited. For example, it can be conducted by dialyzing or water filtering the solution containing fucoidan against an acidic solution and then neutralizing with a solution containing zinc, or by using an ion exchange resin and the like.

The acidic solution used above is not particularly limited, and it can be obtained by, for example, adding an acid such as hydrochloric acid to water to adjust the pH to 1 to 5, preferably 2.5 to 3.5.

The method of dialyzing a solution containing fucoidan against an acidic solution is not particularly limited. For example, a solution containing fucoidan of about 3 mass % may be placed in a dialysis membrane, then placed in an acidic solution of about 10 times or more the volume and stirred overnight. When an ultrafiltration membrane is used instead of the dialysis membrane, water filtration can be conducted.

The alkaline aqueous solution containing the zinc compound used above is prepared by, for example, adding to water a zinc compound which shows alkalinity when dissolved in water. Examples of zinc compounds which show alkalinity when dissolved in water include zinc hydroxide, zinc carbonate and zinc gluconate, and zinc hydroxide and zinc carbonate are preferable. Furthermore, for the amount of the zinc compound contained in the alkaline aqueous solution, it may be added such that the amount of zinc with respect to fucoidan is the above-mentioned amount. The alkaline aqueous solution thus prepared is brought into contact with an acidic aqueous solution containing fucoidan prepared as described above. This contact is carried out in an aqueous solution.

A zinc-bound fucoidan in which zinc is bound to a sulfate group of fucoidan is obtained as described above. In the zinc-bound fucoidan, zinc is 0.1% or more, preferably 0.5% or more, particularly preferably 1% or more with respect to 1 of fucoidan in terms of mass. The binding of zinc to the sulfate group of fucoidan and its amount can be measured by an atomic absorption photometer or ion chromatography.

On the other hand, when the preparation of the invention is a preparation combining fucoidan and zinc, it is good as long as the amounts of fucoidan and zinc are the above amounts. The origin of zinc is not particularly limited and may be a zinc compound such as zinc chloride and zinc glucuronate, or a food or beverage containing zinc such as oyster, meat and liver.

The preparation of the invention may be in the form of powder, granule, liquid or gel, or a beverage, tablet, soft capsule and the like containing these forms.

In preparing the preparation of the invention into the aforementioned forms, for example, vitamin C, citric acid, crystalline cellulose, gelatin, oils such as olive oil, and the like may be contained.

Moreover, the preparation of the invention can be prepared by a known method except that fucoidan and zinc are contained within the above-mentioned ranges in conventionally existing beverages, tablets, soft capsules and the like.

As a preferable embodiment of the preparation of the invention, any preparation will do as long as fucoidan is administered in an amount of 100 mg or more per day, preferably 500 mg per day. As such preparations, the following can be exemplified.

| (1) Tablet | |
|---|---|
| Zinc-bound fucoidan powder (containing 0.1 to 0.3 g of zinc) | 10 g |
| (2) Granule | |
| Fucoidan powder | 10 g |
| Zinc gluconate (containing 0.1 to 0.3 g of zinc) | 1 g |
| (3) Soft capsule | |
| Fucoidan powder | 10 g |
| Oyster extract powder (containing 0.1 to 0.3 g of zinc) | 10 g |
| (4) Beverage | |
| Fucoidan powder | 3 g |
| Zinc gluconate (containing 0.1 to 0.3 g of zinc) | 0.5 g |
| Citric acid | 5 g |
| Water | 500 g |
| (5) Jelly beverage | |
| Fucoidan powder | 0.3 g |
| Zinc sulfate (containing 0.1 to 0.3 g of zinc) | 0.05 g |
| Citric acid | 0.5 g |
| Water | 50 g |
| (6) Supplement | |
| *Lepidium peruvianum* concentration extract powder | 0.2 g |
| *Cordyceps sinensis* extract | 0.05 g |
| Reindeer horn extract | 0.05 g |
| Zinc yeast (containing 0.001 to 0.01 g of zinc) | 0.06 g |
| Fucoidan powder | 0.2 g |

The preparation of the invention has enhanced absorption of fucoidan into the body. However, in the fucoidan which is an active ingredient of the preparation of the invention, the absorption of *Cladosiphon okamuranus* fucoidan into the body can be confirmed by ELISA system utilizing the antibody of *Cladosiphon okamuranus* fucoidan described in JP-B-5764854. For other fucoidans, the absorption into the body can also be confirmed by preparing antibodies according to this method and constructing the ELISA system.

In the preparation of the invention described above, since the absorption of fucoidan into the body is increased by 10 times or more, various effects such as anti-ulcer activity, anti-inflammatory activity, intestine-regulating activity, anti-tumor activity, and cholesterol down-regulation effect of fucoidan are significantly higher than the case where fucoidan is ingested alone.

Therefore, the preparation of the invention is suitable for an anti-ulcer agent, an anti-inflammatory agent, an intestine-regulating agent, an antitumor agent, a cholesterol down-regulation agent and the like. It is also suitable for a food or beverage for promoting effects such as anti-ulcer activity, anti-inflammatory activity, intestine-regulating activity, anti-tumor activity and cholesterol down-regulation effect by blending the preparation of the invention into the food or beverage.

The zinc-bound fucoidan used in the preparation of the invention is a novel compound. By containing it in conventionally known foods or beverages, it can be made into a food or beverage for promoting various effects of fucoidan. Examples of foods and beverages include health foods and nourishing tonics. Among these foods and beverages, foods and beverages not containing fucoidan or zinc are preferable, and foods and beverages not containing fucoidan and zinc are particularly preferable.

EXAMPLES

The invention will be described below in detail with reference to examples. However, the invention is not limited to these examples.

Example 1

Preparation of Zinc-Bound *Cladosiphon okamuranus* Fucoidan:

1 g of *Cladosiphon okamuranus* fucoidan (average molecular weight of 52 kDa: manufactured by South Product Co., Ltd.) was dissolved in 100 ml of ultrapure water (milli Q water). This was dialyzed overnight against 1 liter of a hydrochloric acid solution of pH 3 using a dialysis membrane (manufactured by Spectrum Laboratories) having a cut-off molecular weight of 8,000. After the dialysis, it was confirmed that the pH of the solution was 3 or less, and 0.5 g of zinc hydroxide was added, stirred and dissolved into the solution. After confirming that the pH of the solution became 5 or more, zinc hydroxide not dissolved was removed by centrifugation, and a supernatant was collected and lyophilized to obtain 1 g of powder.

This powder was again dissolved in water to measure the content of *Cladosiphon okamuranus* fucoidan by the anthrone sulfuric acid method (Analytical Chemistry Vol. 10 (1961) No. 1 P64-71) and to measure the average molecular weight by the gel filtration method. As a result, the content of *Cladosiphon okamuranus* fucoidan was 63.2% and the average molecular weight was 54.9 kDa. The zinc content was measured with an atomic absorption photometer and was found to be 235.994 ppm. As a comparison, the zinc content of the raw material *Cladosiphon okamuranus* fucoidan was measured and was found to be 0.615 ppm.

It was found from the above results that the above obtained is a zinc-bound *Cladosiphon okamuranus* fucoidan in which zinc is bound to the sulfate group of *Cladosiphon okamuranus* fucoidan and 2% zinc is bound with respect to *Cladosiphon okamuranus* fucoidan.

Example 2

Preparation of *Cladosiphon okamuranus* Fucoidan Preparation (1):

The zinc-bound *Cladosiphon okamuranus* fucoidan obtained in Example 1 was dissolved in water to be 10 mg/ml to prepare a *Cladosiphon okamuranus* fucoidan preparation (200 ppm of zinc).

Example 3

Preparation of *Cladosiphon okamuranus* Fucoidan Preparation (2):

Zinc chloride was mixed, to be 200 ppm, into an aqueous solution containing 10 mg/ml of *Cladosiphon okamuranus* fucoidan (average molecular weight of 52 kDa: manufactured by South Product Co., Ltd.) to obtain a *Cladosiphon okamuranus* fucoidan preparation.

Test Example 1

Figure 2:
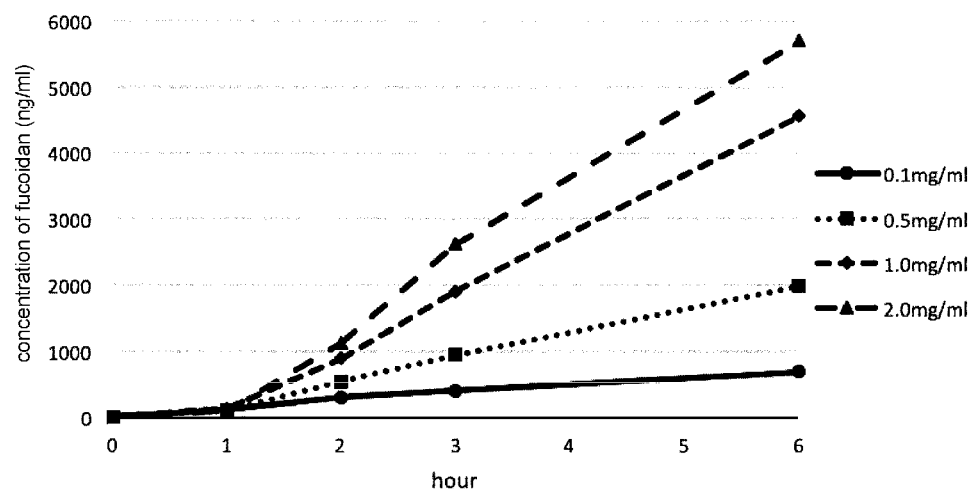
FIG. 2 is a result of absorption test of a *Cladosiphon okamuranus* fucoidan preparation containing a zinc-bound *Cladosiphon okamuranus* fucoidan (Test Example 1).
Figure 3:
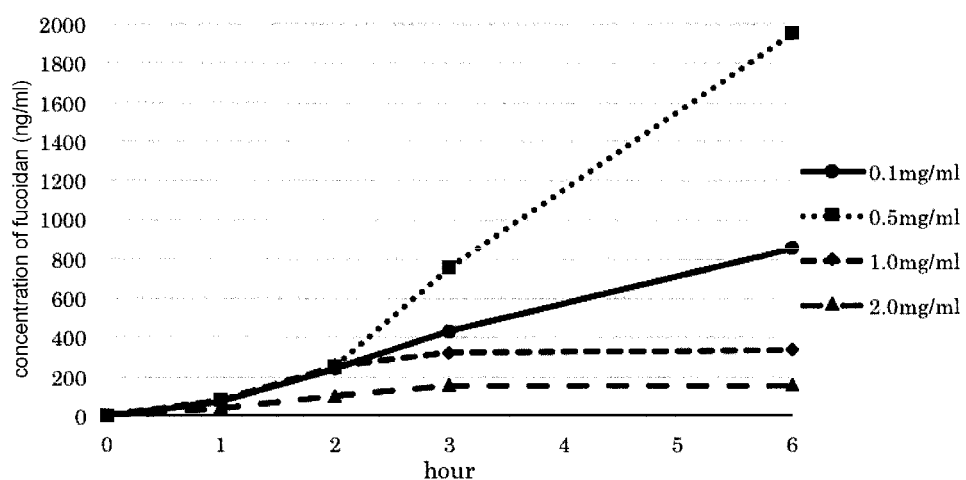
FIG. 3 is a result of absorption test of a *Cladosiphon okamuranus* fucoidan preparation containing *Cladosiphon okamuranus* fucoidan and zinc (zinc chloride) (Test Example 1).

Permeation Test Using Caco2 Cells:

Concentrations of *Cladosiphon okamuranus* fucoidan in the *Cladosiphon okamuranus* fucoidan preparations obtained in Example 2 or Example 3 were adjusted to 0.1 mg/ml, 0.5 mg/ml, 1.0 mg/ml and 2.0 mg/ml respectively, and absorption tests (M. Pinto et al.: Biol. Cell, 47, 323 (1983).) using Caco2 cells (cells derived from human colon carcinoma) were conducted on these preparations. Prior to the absorption tests, a calibration curve of *Cladosiphon okamuranus* fucoidan was prepared using an antibody of *Cladosiphon okamuranus* fucoidan described in JP-B-5764854 (results not shown). As a comparison, the same absorption test was also conducted on *Cladosiphon okamuranus* fucoidan (average molecular weight of 52 kDa: zinc 0.615 ppm: manufactured by South Product Co., Ltd.). The results are shown in FIGS. 1 to 3.

The absorption of *Cladosiphon okamuranus* fucoidan preparations obtained in Example 2 and Example 3 into the body was enhanced as compared with *Cladosiphon okamuranus* fucoidan only. It was found from the result that the absorption of *Cladosiphon okamuranus* fucoidan is enhanced by binding or adding zinc.

Test Example 2

Cytotoxicity Test Using HuH-7 Cells:

Concentrations of *Cladosiphon okamuranus* fucoidan in the *Cladosiphon okamuranus* fucoidan preparations obtained in Example 2 or Example 3 were adjusted to 1 µg/ml, 10 µg/ml, 100 µg/ml and 1000 µg/ml respectively, and MTT assays (Wilson, A. P. (2000). "Cytotoxicity and Viability Assays". In Masters, J. R. W. Animal Cell Culture: A Practical Approach, 3rd) using HuH-7 cells were conducted on these preparations.

Cytotoxicity of HuH-7 cells was confirmed at a concentration of 1000 µg/ml in each of the *Cladosiphon okamuranus* fucoidan preparations obtained in Example 2 and Example 3. However, the effect of the *Cladosiphon okamuranus* fucoidan preparation obtained in Example 2 (containing zinc-bound *Cladosiphon okamuranus* fucoidan) was 1,000 times or more higher than the effect of the *Cladosiphon okamuranus* fucoidan preparation obtained in Example 3 (containing *Cladosiphon okamuranus* fucoidan and zinc).

Example 4

Preparation of Sporophyll-Derived Fucoidan Preparation:

Zinc chloride was mixed, to be 200 ppm, into an aqueous solution containing 10 mg/ml of fucoidan (manufactured by Marui Bussan Co., Ltd.) derived from sporophyll of *Undaria pinnatifida* to obtain a sporophyll-derived fucoidan preparation.

Example 5

Preparation of *Sargassum horneri*-Derived Fucoidan Preparation:

Zinc chloride was mixed, to be 200 ppm, into an aqueous solution containing 10 mg/ml of fucoidan (manufactured by South Product Co., Ltd.) derived from *Sargassum horneri* to obtain a *Sargassum horneri*-derived fucoidan preparation.

Test Example 3

Figure 4:
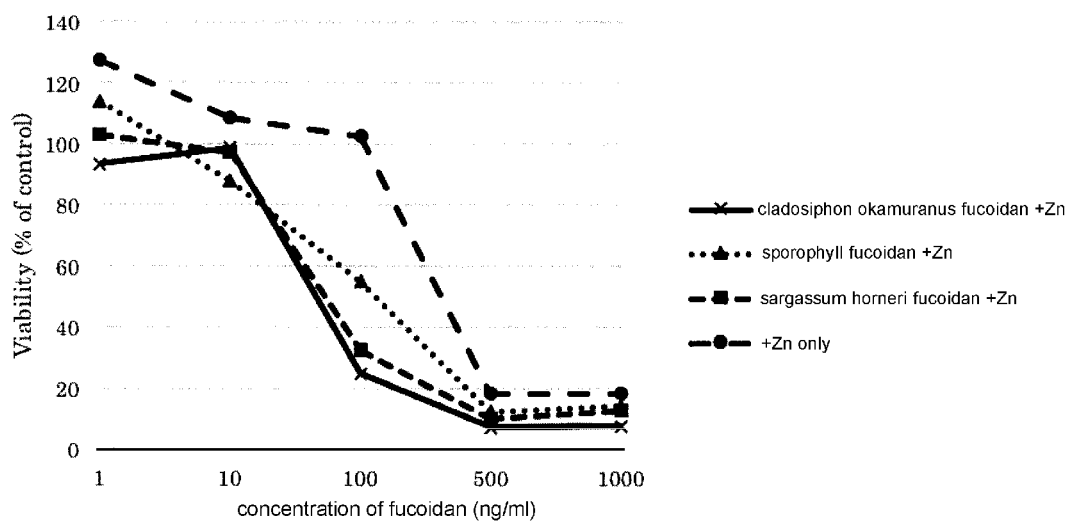
FIG. 4 is a result of cytotoxicity test of Hep G2 using preparations of fucoidan (zinc chloride added) derived from different seaweed (Test Example 3).
Figure 5:
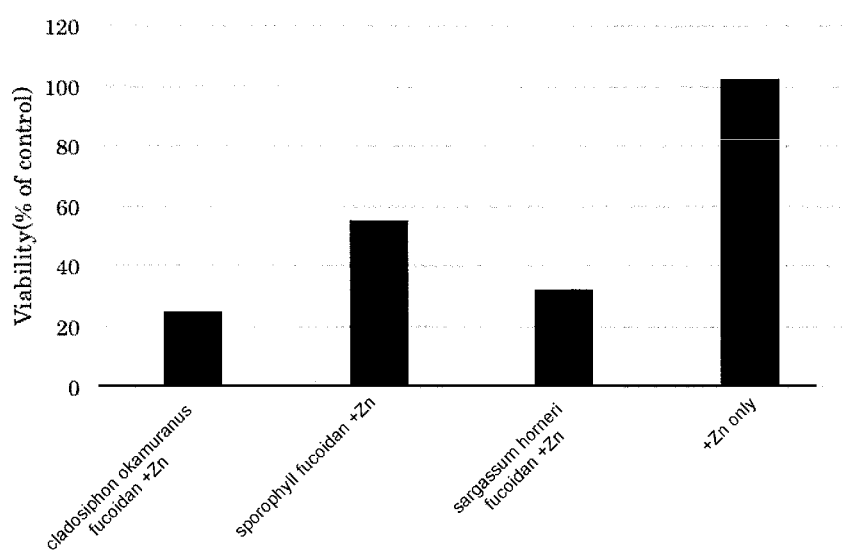
FIG. 5 is viability of Hep G2 cells using preparations of fucoidan (zinc chloride added) derived from different seaweed at a concentration of 100 μg/ml (Test Example 3).

Cytotoxicity Test Using Hep G2 Cells:

Concentrations of fucoidan in the fucoidan preparations obtained in Example 3, Example 4 or Example 5 were adjusted to 1 µg/ml, 10 µg/ml, 100 µg/ml and 1000 µg/ml respectively, and MTT assays (Wilson, A. P. (2000). "Cytotoxicity and Viability Assays". In Masters, J. R. W. Animal Cell Culture: A Practical Approach, 3rd) using Hep G2 cells were conducted on these preparations. The results are shown in FIG. 4. The viability of Hep G2 cells at a concentration of 100 µg/ml is shown in FIG. 5.

Cytotoxicity of Hep G2 cells was confirmed at a concentration of 100 µg/ml in each fucoidan preparation obtained in Example 3, Example 4 or Example 5. However, the effect of the *Cladosiphon okamuranus* fucoidan preparation obtained in Example 3 was higher than the effect of the fucoidan preparation obtained in Example 4 or Example 5. The same test was conducted with zinc only as a comparison, and as a result, no cytotoxicity of Hep G2 cells was confirmed up to 500 µg/ml.

Example 6

Tablet:

10 g of zinc-bound fucoidan powder (containing 0.1 to 0.3 g of zinc) and 90 g of dextrin were mixed and tableted to obtain tablets of 0.2 g per tablet.

Example 7

Granule:

10 g of fucoidan powder, 1 g of zinc gluconate (containing 0.1 to 0.3 g of zinc) and 40 g of crystalline cellulose were mixed and granulated to obtain granules.

Example 8

Soft Capsule:

10 g of fucoidan powder, 10 g of oyster extract powder (containing 0.1 to 0.3 g of zinc) and 80 g of olive oil were mixed and sealed at 0.35 g per pill of soft capsule to obtain soft capsules.

Example 9

Beverage:
3 g of fucoidan powder, 0.5 g of zinc gluconate (containing 0.1 to 0.3 g of zinc) and 5 g of citric acid were dissolved in 500 g of water to obtain a beverage.

INDUSTRIAL APPLICABILITY

The fucoidan preparation of the invention has enhanced absorption into the body and is suitable for obtaining various effects of fucoidan.

The invention claimed is:

1. A fucoidan preparation, comprising:
fucoidan and zinc that is bound to a sulfate group of the fucoidan,
wherein the fucoidan preparation comprises the zinc in 0.005% or more with respect to a total amount of the fucoidan by mass.

2. The fucoidan preparation according to claim 1, wherein the fucoidan is derived from *Cladosiphon okamuranus*.

3. An agent, comprising:
the fucoidan preparation according to claim 1,
wherein the agent is selected from the group consisting of an anti-ulcer agent, an anti-inflammatory agent, an intestine-regulating agent, an antitumor agent, and a cholesterol down-regulation agent.

4. The fucoidan preparation according to claim 1, which is a food or beverage.

5. The fucoidan preparation according to claim 1, which is in the form of a tablet, capsule or granule.

6. The fucoidan preparation according to claim 1, wherein the fucoidan preparation comprises the zinc in 0.1% or more with respect to a total amount of the fucoidan by mass.

7. The fucoidan preparation according to claim 1, wherein the fucoidan preparation comprises the zinc in 0.5% or more with respect to a total amount of the fucoidan by mass.

8. A method for enhancing absorption of fucoidan into a body, comprising:
administering the fucoidan preparation according to claim 1 to a human.

* * * * *